(12) United States Patent
Ba et al.

(10) Patent No.: US 10,562,937 B2
(45) Date of Patent: *Feb. 18, 2020

(54) ELECTRON SPIN LABELED ICE BINDING COMPOUNDS USED FOR CARRYING PARAMAGNETIC CENTERS FOR DYNAMIC NUCLEAR POLARIZATION

(71) Applicant: The Trustees of California State University, Los Angeles, CA (US)

(72) Inventors: Yong Ba, Monrovia, CA (US); Yougang Mao, Monterey Park, CA (US)

(73) Assignee: The Trustees of California State University, Los Angeles, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 15/652,036

(22) Filed: Jul. 17, 2017

(65) Prior Publication Data

US 2018/0044382 A1 Feb. 15, 2018

Related U.S. Application Data

(60) Continuation of application No. 15/014,978, filed on Feb. 3, 2016, now Pat. No. 9,738,686, which is a
(Continued)

(51) Int. Cl.
*C07K 14/00* (2006.01)
*C07K 14/46* (2006.01)
(Continued)

(52) U.S. Cl.
CPC .............. *C07K 14/00* (2013.01); *A61K 49/00* (2013.01); *A61K 49/14* (2013.01); *C07K 14/46* (2013.01)

(58) Field of Classification Search
None
See application file for complete search history.

(56) References Cited

U.S. PATENT DOCUMENTS

| 7,985,594 B2 | 7/2011 | Griffin et al. |
| 2008/0260649 A1 | 10/2008 | Thaning et al. |
| 2016/0207962 A1 | 7/2016 | Ba et al. |

OTHER PUBLICATIONS

Ned Van Eps et al.; "EPR Studies of Functionally Active, Nitroxide Spin-Labeled Peptide Analogs of the C-terminus of a G-Protein Alpha Subunit"; Biochemistry; 2010; pp. 6877-6886.
(Continued)

*Primary Examiner* — Xiaoyun R Xu
(74) *Attorney, Agent, or Firm* — Andrew D. Fortney; Central California IP Group, P.C.

(57) ABSTRACT

Spin-labeled ice binding compounds (IBCs) including ice binding proteins (IBPs) or antifreeze proteins (AFPs) and their analogs may carry paramagnetic centers for dynamic nuclear polarization (DNP), for enhancing nuclear magnetic resonance (NMR) signal intensities. Use of spin-labeled IBCs to perform DNP exploits the IBCs' ability to homogeneously distribute the paramagnetic centers in frozen water solution at low temperature, leading to high DNP efficiency. Other advantages of using spin-labeled IBCs include cryo-protecting biological samples; cryo-preserving relative positions and orientations of the spin labeling groups; selecting positions and orientations of spin labeling groups with freedom and without technical barriers to making multiple spin labels in an IBC; and enabling use of a solvent that is primarily water for DNP at low temperatures in view of the potentially high water solubilities of spin-labeled IBCs.

20 Claims, 8 Drawing Sheets

Specification includes a Sequence Listing.

Related U.S. Application Data division of application No. 13/551,482, filed on Jul. 17, 2012, now abandoned.

(60) Provisional application No. 61/509,107, filed on Jul. 18, 2011.

(51) Int. Cl.
*A61K 49/00* (2006.01)
*A61K 49/14* (2006.01)

(56) References Cited

OTHER PUBLICATIONS

Sarah L. Buckley and Peter J. Lillford; "Antifreeze Proteins: Their Structure, Binding and Use"; Modern Biopolymer Science; 2009; Elsevier Inc.; pp. 93-128.

Okkes Atici and Barbaros Nalbantoglu; "Antifreeze Proteins in Higher Plants"; Phytochemistry; 2003; Pergamon; vol. 64; pp. 1187-1196.

Peter L. Davies and Brian D. Sykes; "Antifreeze Proteins"; Current Opinion in Structural Biology; 1997; Current Biology Ltd.; pp. 828-834.

Kalman Hideg and Olga H. Hankovszky; "Chemistry of Spin-Labeled Amino Acids and Peptides"; Biol. Magn. Resonance 8; 1989; Plenum Press; pp. 427-487.

Barbara Moffatt et al.; "Cold Comfort: Plant Antifreeze Proteins"; Physiologia Planatarum; 2006; pp. 5-16.

Thorsten Maly et al; "Dynamic Nuclear Polarization at High Magnetic Fields"; 20 pgs.; The Journal of Chemical Physics; 2008; American Institute of Physics; vol. 128, 052211.

Heman Chao et al; "Effects of Antifreeze Proteins on Red Blood Cell Survival During Cryopreservation"; The Journal of Experimental Biology; 1996; The Company of Biologists Ltd.; vol. 199; pp. 2071-2076.

Melody L. Mak-Jurkauskas and Robert G. Griffin; "High-Frequency Dynamic Nuclear Polarization"; Solid-State NMR Studies of Biopolymers; 2010; John Wiley and Sons; pp. 159-174.

A. Baguisi et al; "Hypothermic Storage of Sheep Embryos with Antifreeze Proteins Development in Vitro and in Vivo"; Theriogenology; Elsevier Science, Inc.; 1997; pp. 1017-1024.

Rolf Mehlhorn et al; "An Imidoester Spin Probe of Membrane Protein Interactions: Application to Cytochrome c"; Archives of Biochemistry and Biophysics; vol. 204, No. 2, Oct. 15, 1980; pp. 471-476.

O.H. Hankovszky et al; "New Nitroxide Reagents for the Selective Spin-Labelling at the Guanidino Moiety of Arginine Residues in Peptides and Proteins"; Elsevier Science Publishers B.V. (Biomedical Division); 1987; pp. 57-82.

S. Venketesh and C. Dayananda; "Properties, Potentials, and Prospects of Antifreeze Proteins"; Crit. Rev. Biotechnol.; Informa Healthcare USA, Inc.; 2008; pp. 57-82.

Wayne L. Hubbell et al; "Recent Advances in Site-Directed Spin Labeling of Proteins"; Current Opinion in Structural Biology; Current Biology Ltd.; 1998; pp. 649-656.

Luis Galiano et al; "Solute Effects on Spin Labels at an Aqueous-Exposed Site in the Flap Region of HIV-1 Protease"; Journal of Physical Chemistry B; vol. 113; 2009; pp. 1673-1680.

T.N. Hansen et al; "Type I Antifreeze Protein Attenuates Cell Recoveries Following Cryopreservation"; 4 pgs.; Transplantation Proceedings; vol. 25, No. 6; Dec. 1993; pp. 3182-3184.

FIGS. 1(A)-(D)
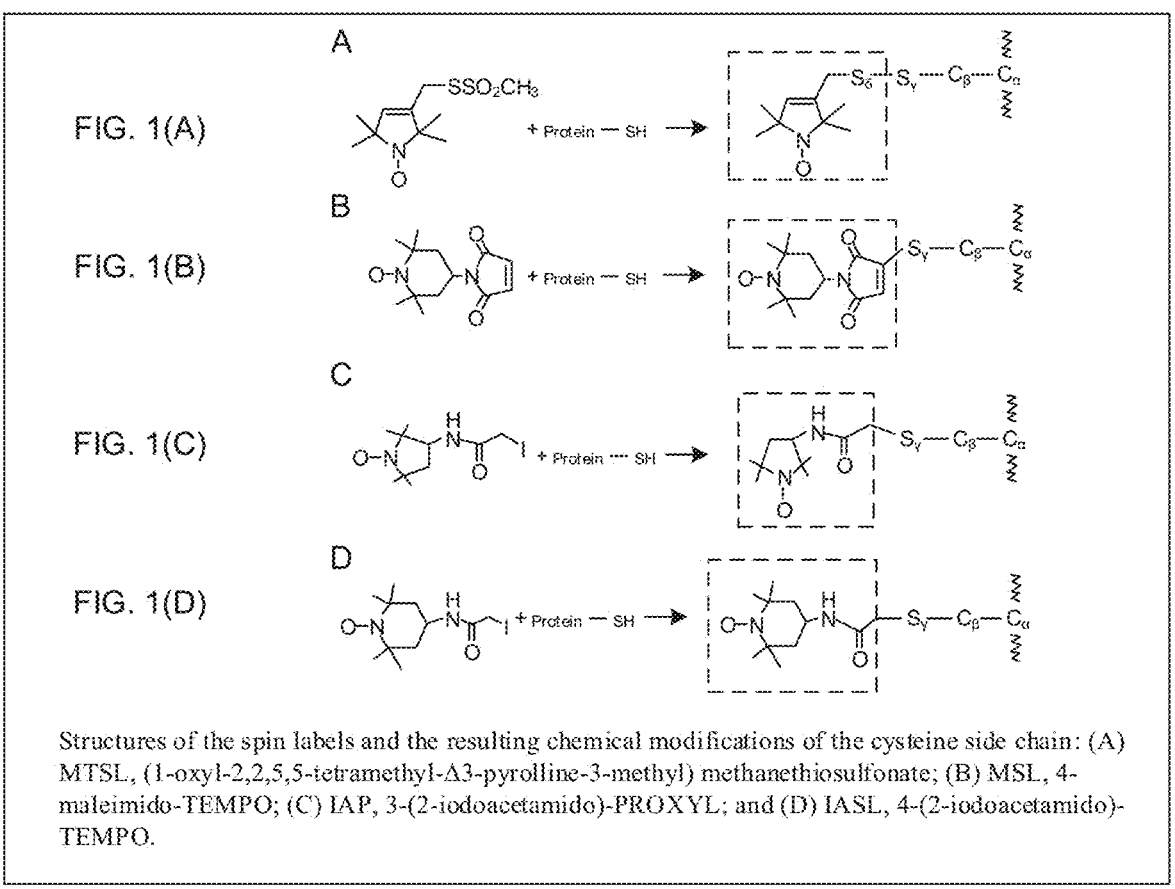
Structures of the spin labels and the resulting chemical modifications of the cysteine side chain: (A) MTSL, (1-oxyl-2,2,5,5-tetramethyl-Δ3-pyrolline-3-methyl) methanethiosulfonate; (B) MSL, 4-maleimido-TEMPO; (C) IAP, 3-(2-iodoacetamido)-PROXYL; and (D) IASL, 4-(2-iodoacetamido)-TEMPO.

FIG. 2(A)

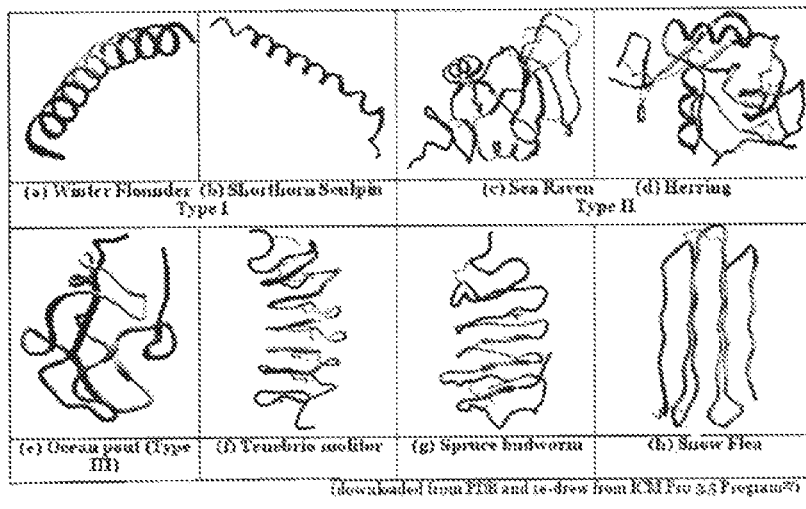

General structures of several types of AFPs.

FIG. 2(B)

|  | Species | PDB ID | No. of residue | Structure type | Size (KDa) | Residues Repeat |
|---|---|---|---|---|---|---|
| Fish AFPs | | | | | | |
| Type I | Winter Flounder | 1WFA | 37 | α-helix; Ala-rich | 3-5 | 11aa |
|  | Shorthorn Sculpin | 1Y03 | 35 | | | |
| Type II | Sea Raven | 2AFP | 129 | Globular; Ca²⁺ dependent; mixed α, β and loop structure | 14-24 | None |
|  | Herring | 2PY2 | 127 | | | |
| Type III | Ocean pout | 1MSI | 64 | Globular; one flattened surface; short β strands | 7 | None |
| Insect AFPs | | | | | | |
|  | Spruce budworm | 1EWW | 90 | Left-handed β-helix | 9 | 15aa |
|  | Snow Flea | 2PNE | 81 | Glycine-rich | 6.5-15.7 | 2?aa |
|  | Tenebrio molitor | 1L1I | 84 | Right-hand β-helix | 8.4 | 12aa(TCTxS xxCxxAx) |

Typical structural data of the given APFs.

FIGS. 3(A)-(F)
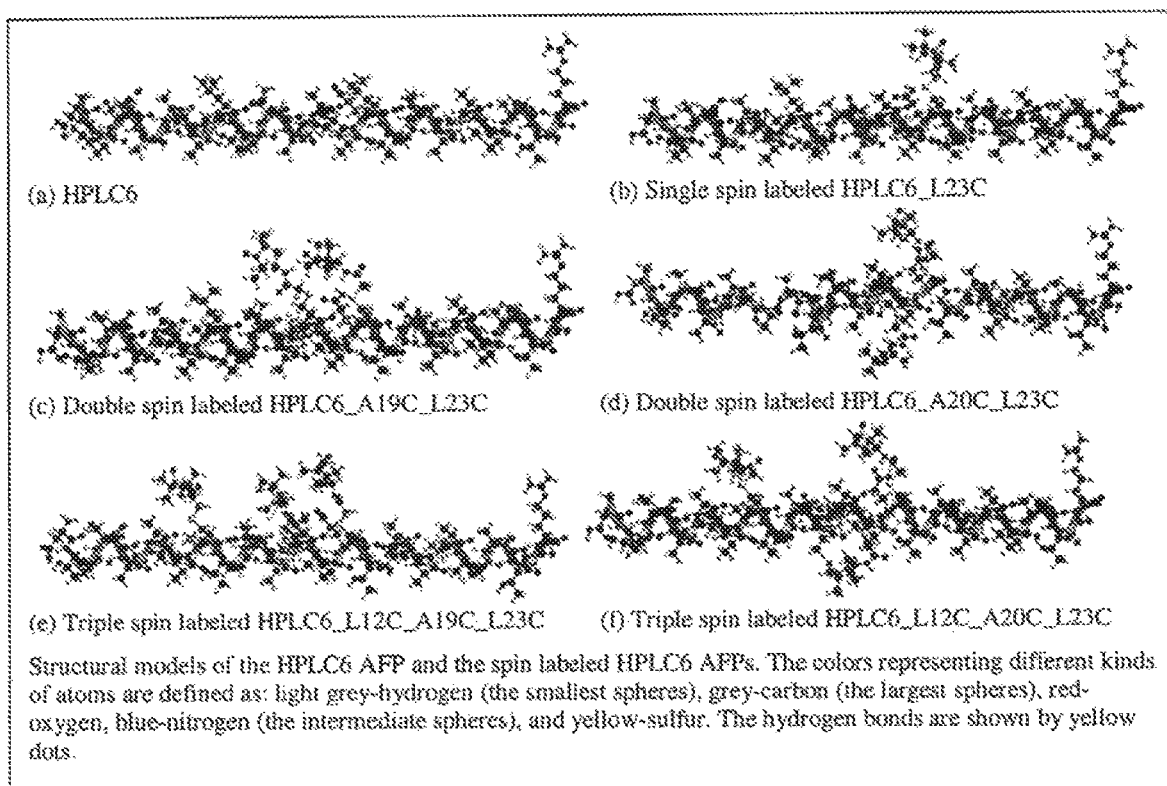

(1) Trityl  (2) BDPA  (3) Tempo  (4)  (5) Proxyl

Examples of free radical groups. (The chemical name of (4) is 1-oxyl-2,2,5,5-Tetramethyl-3-pyrroline)

Structures of TEMPO-based biradicals. (Adapted from *Mak-Jurkauskas ML, Griffin RG: High-frequency dynamic nuclear polarization. In: 2010: John Wiley & Sons Ltd.; 2010: 159-174.*)

Functional groups in a peptide or protein that can be used to perform spin labeling.

FIGS. 8(A)-(B)

Structures of 3-(2-iodoacetamido)-DTPA (a) and its $Gd^{3+}$ complex (b).

ELECTRON SPIN LABELED ICE BINDING COMPOUNDS USED FOR CARRYING PARAMAGNETIC CENTERS FOR DYNAMIC NUCLEAR POLARIZATION

RELATED APPLICATION(S)

This application is a continuation of U.S. patent application Ser. No. 15/014,978, filed Feb. 3, 2016, pending, which is a divisional of U.S. patent application Ser. No. 13/551,482, filed Jul. 17, 2012, abandoned, which claims priority to U.S. Provisional Pat. Appl. No. 61/509,107, filed Jul. 18, 2011, which is incorporated herein by reference in its entirety.

FEDERAL FUNDING STATEMENT

This work was supported by NIH Grant 5SC1 GM083826-04.

BACKGROUND

The present invention relates generally to methods and compositions for performing dynamic nuclear polarization (DNP), and for further performing Nuclear Magnetic Resonance (NMR) and Magnetic Resonance Imaging (MM) using the compounds so produced. NMR has become an irreplaceable tool in the studies of macromolecular structures, dynamics, and interactions, such as in the studies of proteins, DNA, their complexes, and also in imaging tissue structures. However, a major bottle neck of NMR for high throughput applications is its low sensitivity. The intrinsic reason for low sensitivity arises from the low equilibrium polarization of Boltzmann populations at different energy levels of nuclear spins in an external magnetic field. The equilibrium polarization is proportional to the strength of the external magnetic field and inversely proportional to the absolute temperature of the sample. Thus, to increase the polarization, one can either increase the strength of the external magnetic field, decrease the sample temperature, or do both.

To date, the highest field of commercially available magnet is ~23.5 Tesla (corresponding to proton magnetic resonance frequency ~1 GHz). To increase the magnetic field strength of the highest commercial magnet even by two-fold (to 47 Tesla) cannot currently be technologically and/or financially foreseen. Another way to handle the problem of low sensitivity is to develop more sensitive instruments to detect NMR signals. For example, CryoProbe™ devices developed in recent years have been able to increase NMR sensitivity up to four-fold. Cryoprobe™ device technology deals with suppressing the instrumental thermal noises by reducing the temperature of the NMR coil and preamplifier using cold helium gas at ~20 K. In order to tremendously increase the NMR signal intensities, other technologies and methods have yet to be developed.

A promising approach to increasing NMR sensitivity is to dynamically polarize the nuclear spins of the samples. If a sample contains either exogenous or endogenous paramagnetic centers, such as paramagnetic metal ions (including transition, actinide, and lanthanide metal ions), nitroxide radicals, and trityl radicals, for example, irradiation of the paramagnetic centers in a magnetic field can lead to dynamic polarization of the nuclear spins. In principle, this technique can enhance the proton signal by 660-fold and that of $^{13}C$ by 2600-fold due to the gyromagnetic ratios of electron to nuclei ($\gamma_e/\gamma_n$) of proton and $^{13}C$, respectively. Use of dinitroxide-type biradical compounds for dynamic nuclear polarization (DNP) previously has been described. A factor of signal enhancement of 175-fold was achieved. The DNP experiments are carried out at temperatures 100 K in order to suppress the electronic and nuclear spin lattice relaxation rates to favor the polarization transfer. At such a low temperature, a solvent is required for homogenous distribution of the paramagnetic centers in the frozen solution for effective polarization distribution throughout the sample. The most commonly used solution is a 40:60 v/v mixture of water:glycerol, which forms a glassy matrix at low temperature regardless of the cooling rate. Biological samples are also expected to be cryo-protected using this solvent.

Despite the achievement of the DNP experiments, one drawback is the use of the mixture of water and glycerol as the solvent. This solvent requirement may limit many biological applications because in almost all of the studies of biomolecules, water represents the sole environment to mimic the behaviors and structures of biomolecules as in living cells. This invention addresses the issue of using water as the primary solvent for DNP at low temperatures through the use of electron spin-labeled ice binding compounds (IBCs).

SUMMARY OF THE INVENTION

It has now been discovered that electron spin, or "spin" (including single spin, multiple spin, and paramagnetic ion) labeled ice binding compounds (IBCs), including ice binding proteins (IBPs) and antifreeze proteins (AFPs) may be used to homogeneously distribute paramagnetic centers (the assemblies of the electron spins) in frozen water solution for DNP. For the purposes of this disclosure, the terms "IBP" and "AFP" will be used interchangeably, and include naturally occurring and synthetic forms, as well as complexes having other compounds chemically connected to IPBs or AFPs, for example, peptides, proteins and other nonproteinaceous compounds. These terms are meant to also include any other organic and/or inorganic compounds that have similar ability to bind to ice surfaces (ice binding compounds, "IBCs"). Also included are multiple complexes, for example, dimers.

IBPs provide protection for organisms that express AFPs living through subzero winters from freezing damage due to their property to bind to specific ice surfaces, thereby inhibiting growth of seed ice crystals and the recrystallization of ice crystals. The ice binding property allows the homogeneous dispersion of IBPs in frozen aqueous solutions, primarily aqueous solutions, and also other solutions that form glassy solids at low temperature. The terms "primarily aqueous," "primarily water," and the like terms are meant to refer to solutions in which the majority constituent is water. Therefore, after electron spins are labeled to the non-ice-binding side chains of IBPs, the paramagnetic centers can be homogeneously distributed in frozen solution which can serve for effectively polarizing the nuclear spins in the frozen solution. The term "frozen solution" is meant to include aqueous solutions, primarily aqueous solutions, and other solutions wherein glassy solids form at low temperatures. This approach may allow broad applications of DNP, especially for the study of biomolecular structures and tissue structures where the solution is water. However, it is contemplated that the spin-labeled IBPs will also have application for analyses of non-biological compounds.

Other underlying rationales for using spin-labeled IBPs to perform DNP include: (1) IBPs have the ability to cryo-protect biological samples; (2) the structures of IBPs are naturally cryo-protected at low temperature enabling the relative positions and orientations of the spin-labeling groups in an IBP to also be cryo-preserved; (3) using site-directed mutagenesis techniques, the positions and orientations of the spin-labeling groups to an IBP can be selected with great freedom and there is no technical barrier to making multiple spin labels in an IBP; and (4) water solubilities of the spin-labeled IBPs are potentially high.

BRIEF DESCRIPTION OF THE DRAWINGS

FIGS. 1A-1D show structures of exemplary spin labels and resulting chemical modifications of cysteine side chains. FIG. 1(A) shows MTSL, (1-oxyl-2,2,5,5-tetramethyl-Δ3-pyrroline-3-methyl)methanethiosulfonate; FIG. 1(B) shows MSL, 4-maleimido-TEMPO; FIG. 1(C) IAP, 3-(2-iodoacetamido)-PROXYL; and FIG. 1(D) IASL, 4-(2-iodoacetamido)-TEMPO.

FIG. 2A shows the general structures of several types of AFPs.

FIG. 2B shows the typical structural data of several types of AFPs.

FIGS. 3(A)-3(F) show the structural models of the HPLC6 AFP in relation to various spin-labeled HPLC6 AFPs. FIG. 3(A) shows a structural model for HPLC6 AFP. FIG. 3(B) shows a structural model for a single spin-labeled HPLC6_L23C. FIG. 3(C) shows a structural model for a double spin-labeled HPLC6_A19C_L23C. FIG. 3(D) shows a structural model for a triple spin-labeled HPLC6_A20C_L23C. FIG. 3(E) shows a structural model for a triple spin-labeled HPLC6_L12C_A19C_L23C. FIG. 3(F) shows a structural model for a triple spin-labeled HPLC6_L12C_A20C_L23C.

DETAILED DESCRIPTION

Figure 4:
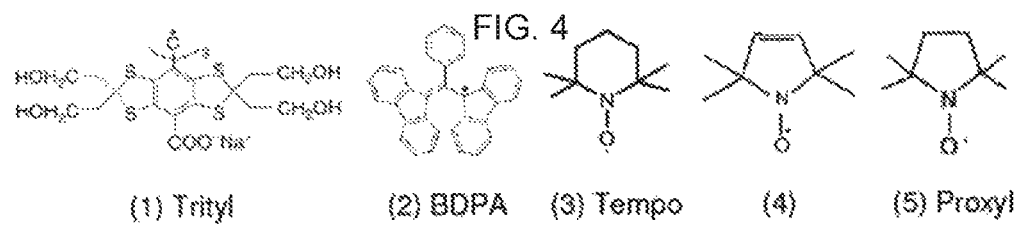
FIG. 4 shows examples of free radical groups.

Throughout this specification, the terms "a" and "an" and variations thereof represent the phrase "at least one." In all cases, the terms "comprising", "comprises" and any variations thereof should not be interpreted as being limitative to the elements listed thereafter. Unless otherwise specified in the description, all words used herein carry their common meaning as understood by a person having ordinary skill in the art. In cases where examples are listed, it is to be understood that combinations of any of the alternative examples are also envisioned. The scope of the invention is not to be limited to the particular embodiments disclosed herein, which serve merely as examples representative of the limitations recited in the issued claims resulting from this application, and the equivalents of those limitations.

Site Directed Spin Labeling (SDSL)

Site Directed Spin Labeling (SDSL) is often accomplished by cysteine-substitution mutagenesis, followed by modification of the unique sulfhydryl group with selective nitroxide or other reagents. FIGS. 1(A)-1(D) give examples of spin-labeling reagents and their chemical reactions with a sulfhydryl group. In FIGS. 1(A)-1(D), Cys-substitution mutants of AFPs are used to provide examples of spin-labeled AFPs.

Presently, five types of fish AFPs have been discovered, including antifreeze glycoprotein (AFGP) and type I, II, III and IV AFPs. AFPs also have been found in insects such as *Tenebrio molitor*, spruce budworm, and snow flea, and in plants such as winter rye (*Secale cereale* L.) and ryegrass (*Lolium perenne*). Although AFPs have different structures and were found in diversified species, they all display similar antifreeze function by binding to specific surfaces, and preventing the growth of seed ice crystals at subzero environment. Thus, other compounds with similar functional capabilities are contemplated as similarly useful for the methods disclosed herein and they are also included within the scope of IBCs. A summary of typical structures of several AFPs are given in FIG. 2A and FIG. 2B.

Single Spin-Labeled AFPs

As an example, the HPLC6 isoform of type I AFP has an α-helical secondary structure (see FIG. 3(A)) and contains three 11-residue repeat units commencing with Thr residues. It has the following sequence: Asp-Thr-Ala-Ser-Asp-Ala-Ala-Ala-Ala-Ala-Ala-Leu(12)-Thr-Ala-Ala(15)-Asn-Ala-Lys-Ala-Ala(20)-Ala-Glu-Leu(23)-Thr-Ala-Ala-Asn-Ala-Ala-Ala-Ala-Ala-Ala-Ala-Thr-Ala-Arg [SEQ ID NO:1], where the ice binding residues are underlined and the residues preferred for substitution with Cys are bolded and numbered (according to the order of the sequence). The corresponding single Cys-substitution mutants are named as: (1) HPLC6_L12C; (2) HPLC6_A15C; (3) HPLC6_A20C; and (4) HPLC6_L23C, where, for example, the L23C denotes that the L residue at position 23 is replaced by a C residue. These Cys substituted residues are not in the ice binding surface (IBS) and located around the mid-section of the α-helical structure. The reason for replacing the L12 or L23 residues with a Cys residue is that Leu side chains are bulky and hydrophobic. Thus, the spin-labeling group at these positions may cause less perturbation to the secondary structure and to the function of the AFP. The side chain of the C23 residue directly points to the opposite direction with respect to the IBS (ice binding surface). The side chains of C20 and C15 point to the two opposite side directions. Other choices of residues for making spin-labeled AFPs are also possible and would be readily apparent in view of the disclosures herein.

Spin labels may be attached to Cys side chains according to standard procedures (FIGS. 1(A)-1(D)). Briefly, AFPs are buffer-exchanged (HiPrep 26/10 Desalting Column, Amersham) into 10 mM Tris, pH 6.9, for the MTSL spin-labeling reaction, or into 10 mM HEPES, pH 7.6, for IAP, IASL, and MSL reactions. Spin labels are dissolved into 100% ethanol and added to the AFP solution at a 100:1 label/Cys-site concentration to ensure complete labeling. The labeling reaction proceeds overnight in darkness at 4° C. After the reactions, excess spin labels are separated using a size-exclusion chromatography equilibrated in acetate buffer (2 mM NaOAc, pH 5.0), or by using a dialysis method. The purified spin-labeled AFP is stored at −20° C. A structural model using the IAP reagent (FIG. 1(C)) to make a single spin-labeled AFP at the C23 side chain is given in FIG. 3(B) as an example.

The Overhauser Effect (OE) was originally proposed to enhance nuclear spin's polarization from that of electron spins. OE involves the simultaneous transitions of an electron spin and a nuclear spin driven by relaxation processes induced by time-dependent dipolar and/or scalar electron-nuclear couplings. However, the efficiency of the OE is lowered dramatically at higher magnetic fields because $\omega_0\tau_c<1$ must be satisfied, where $\omega_0$ is the electron Larmor frequency and $\tau_c$ is the rotational correlation time of the molecules. Thus, it is necessary to find other DNP mechanisms to enhance the nuclear spin's polarization at high magnetic fields for enhancing the signals of modern NMR and MRI.

One of the DNP mechanisms is the Solid Effect (SE), which is a two-spin process. Single spin-labeled IBPs facilitate this mechanism. Microwave irradiation at $\omega_{0S}\pm\omega_{01}$, where $\omega_{0S}$ and $\omega_{01}$ respectively denote the electronic and nuclear Larmor frequencies, can excite the partially allowed electron-nucleus transitions. For the SE to be effective, the inhomogeneous breadth ($\Delta$) and the homogeneous linewidth ($\delta$) of the Electron Paramagnetic Resonance (EPR) spectrum should be much smaller than the nuclear Larmor frequency ($\pm\omega_{01}>\Delta, \delta$) so that only one of the two forbidden transitions can be excited at a time to avoid cancellation. Additionally, the transition probability has a frequency dependence as $1/(\omega_{01})^2$. Thus, the SE's efficiency will decrease quickly with the increase of the magnetic field, resulting in poorer efficiency at high field. Two readily available radicals that have sufficiently narrow linewidths are bisdiphenylene-β-phenyl allyl (BDPA) and trityl (FIG. 4). At 5 T they have spectral breadth of ~20 and ~90 MHz, respectively, which are smaller than the IH Larmor frequency $\omega_{01}$=211 MHz. Conjugation of a single radical of one of these two radicals to an IBP is anticipated to function better than the nitroxide radicals through the SE mechanism for DNP in frozen solutions.

Double Spin-labeled AFPs

SDSL can also be used to make double spin-labeled AFPs. In the following HPLC6 sequence: Asp-<u>Thr</u>-Ala-Ser-Asp-<u>Ala</u>-Ala-Ala-Ala-<u>Ala</u>-Ala-Leu-<u>Thr</u>-Ala-Ala-Asn-<u>Ala</u>-Lys-Ala(19)-Ala(20)-<u>Ala</u>-Glu-Leu(23)-Thr-Ala-Ala-Asn-<u>Ala</u>-Ala-Ala-Ala-Ala-Ala-Thr-Ala-Arg [SEQ ID NO:1], the preferred residues selected for double Cys substitutions are bolded and numbered. These residues are not in the IBS and are located around the mid-section of the a-helix. For example, the following double Cys-substitution mutants can be designed: (1) HPLC6_A19C_L23C; (2) HPLC6_A20C_L23C; and (3) HPLC6_A19C_A20C.

To make double spin-labeled IBPs, spin labels are attached to the Cys side chains according to the standard procedures (FIGS. 1(A)-1(D)). In the foregoing mutants, the side chain of the C23 residue directly points to the opposite direction with respect to the ice surface, that of the C20 points to a side direction, and that of the C19 points roughly to a direction above the ice surface. The distance between the two β-carbons ($C_\beta$) in C20 and C23 is ~5.7 Å, between those in C19 and C23 is ~6.5 Å, and between the C19 and the C20 is ~5.3 Å. All these conditions may result in favored radical-to-radical distances and orthogonal relative orientations of the two π systems in the pairs of nitroxide groups as those of the TOTAPOL as described in the art. Examples of structural models using the IAP reagent (FIG. 1(C)) to make double spin-labeled HPLC6_A19C_L23C and HPLC6_A20C_L23C IBPs are given in FIGS. 3(C) and 3(D).

Figure 5:
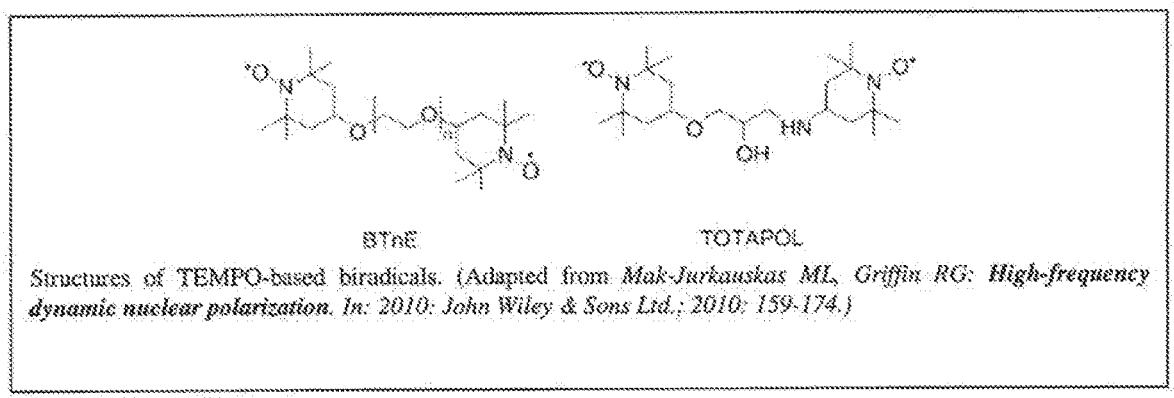
FIG. 5 shows structures of TEMPO-based biradicals. (Adapted from Mak-Jurkauskas ML, Griffin RG: High-frequency dynamic nuclear polarization. In: 2010: John Wiley & Sons Ltd.; 2010: 159-174.)

Another DNP mechanism is the Cross Effect (CE). The double spin-labeled IBPs facilitate the CE, which involves two electrons that are in close physical proximity in order to be effectively dipolarly coupled. To have the CE, the difference of the two EPR frequencies should match the nuclear frequency ($\omega_{0S1}-\omega_{0S2}=\omega_{01}$). The CE is the dominant mechanism in the regime $\Delta>\omega_{01}>\delta$. When two transitions matching the condition above, one from an inhomogeneous line broadening packet $\Delta_1$ and the other from the other $\Delta_2$, the frequency difference of the two transitions goes into polarizing the nuclear spins. This mechanism is a three-spin process and is based on allowed EPR transitions which exhibit a $1/(\omega_{01})$ field dependence. Therefore, the CE is more efficient than the SE. Examples of biradicals that support CE are shown in FIG. 5. An enhancement of ~175 was obtained at electron concentration of 10 mM. To match the condition ($\omega_{0S1}-\omega_{0S2}=\omega_{01}$), the relative orientations of the nodal planes of the π systems of the two nitroxide groups should be nearly orthogonal.

Multiple Spin-labeled AFPs

SDSL can also be used to make triple and multiple spin-labeled AFPs. In the following HPLC6 sequence: Asp-Thr-Ala-Ser-Asp-Ala-Ala-Ala-Ala-Ala-Ala-Leu(12)-Thr-Ala-Ala-Asn-Ala-Lys-Ala(19)-Ala(20)-Ala-Glu-Leu(23)-Thr-Ala-Ala-Asn-Ala-Ala-Ala-Ala-Ala-Ala-Thr-Ala-Arg [SEQ ID NO:1], the preferred residues selected for Cys substitutions are bolded and numbered. These residues are not in the IBS and located around the mid-section of the α-helix. For example, the following Cys-substitution mutants can be designed:
Triple Cys-substitution mutants: (1) HPLC6_L12C_A19C_L23C; (2) HPLC6_L12C_A20C_L 23C; (3) HPLC6_L19C_A20C_L23C; and (4) Quadruple Cys-substitution mutant: HPLC6_L 12C_A19C_A20C_L23C.

In addition to the distances between the pairs of β-carbons in the double Cys substituted mutants, the distance between the C12 $C_\beta$ and C23 $C_\beta$ is ~16.6 Å, that between the C12 $C_\beta$ and C20 $C_\beta$ is ~12.8 Å, and that between the C12 $C_\beta$ and C19 $C_\beta$ is ~10.5 Å. To make the multiple spin-labeled IBPs, the spin labels are attached to the Cys side chains according to the standard procedures (FIGS. 1(A)-1(D)). Structural models using the IAP reagent (FIG. 1(C)) to make the triple spin-labeled HPLC6_L12C_A19C_L23C and HPLC6_L12C_A20C_L23C IBPs are given in FIG. 3(E) and FIG. 3(F) as examples. A similar strategy can be applied to make other triple and multiple spin-labeled IBPs. To perform multiple spin labeling, larger AFPs than the type I AFPs have the advantage of being able to be attached with more nitroxide radicals without significant perturbation to the structures and functions.

Another DNP mechanism is Thermal Mixing (TM). Multiple spin-labeled AFPs facilitate the TM effect, which involves multiple electron spins and the EPR spectrum is homogeneously broadened. The conditions under which the TM is the dominant mechanism are $\Delta>\omega_{01}, \delta$.

Using the Native Functional Side Chains of Proteins to Make Spin-labeled IBPs

The native functional side chains in IBPs may also be used for spin-labeling. This method does not require Cys-substitution mutagenesis. However, the choices for selecting the spin-labeled sites may be more limited by the available functional side chains. Examples of functional groups in the side chains in peptides or proteins that can be used to perform spin labeling are listed in FIG. 6. They contain (but are not limited to) the N-terminus and C-terminus, and the side chains of cysteine, serine, threonine, tyrosine, lysine, aspartic acid, glutamic acid, histidine, tryptophan and arginine. A summary of spin labeling chemistry for spin labeling these residues can be found in Biological Magnetic Resonance 8: Spin Labeling Theory and Applications, Chapter 9

Chemistry of Spin-Labeled Amino Acids and Peptides (K. Hideg and O. H. Hankovszky), Plenum Press, New York and London, pp. 427-487, which is incorporated by reference herein in its entirety. It should be appreciated that departures from the methods described therein would be considered routine and within the ordinary skill of the art.

Other Spin-labeled Compounds Having the Ability to Bind to Ice Surfaces for DNP

Figure 6:
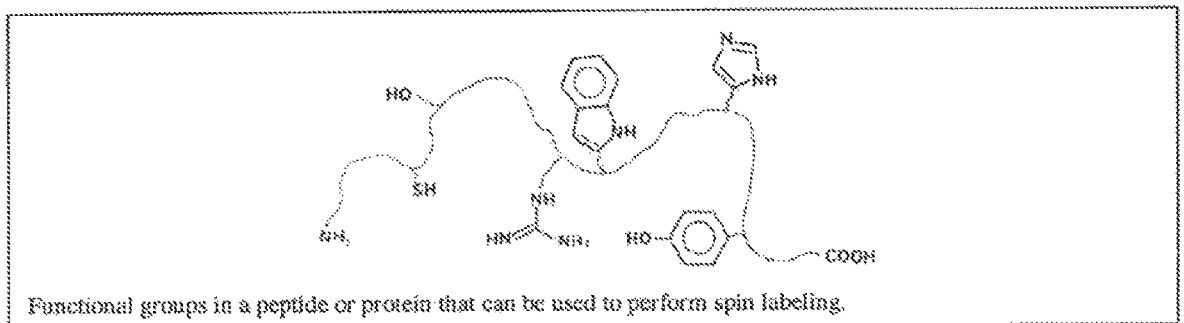
FIG. 6 shows functional groups in a peptide or protein that can be used to perform spin labeling.

Other compounds that are not peptides or proteins but that may be the complexes of peptides or proteins, and organic and/or inorganic molecules, any of which possess ice binding properties and have functional side chains as described in the sections "Site Directed Spin Labeling (SDSL)" and FIGS. 1(A)-1(D), and in the section "Strategy to use the native functional side chains of proteins to make spin-labeled IBPs" and FIG. 6, can be spin-labeled using the methods described herein. These spin-labeled compounds can be used as the paramagnetic centers for DNP, and may be especially useful in primarily water solutions.

Using Free Radicals for Synthesizing Paramagnetic Centers for DNP

Compounds containing stable free radicals (which contain unpaired electron spins) that can be used to perform spin labeling of IBPs include, but are not limited to those given in FIG. 4. A single compound can also contain more than one radical or spin. These structures with chemical bonding to extra functional groups, for instance, as those described in the section "Site Directed Spin Labeling (SDSL)" and FIGS. 1(A)-1(D), and in section "Strategy to use the native functional side chains of proteins to make spin-labeled IBPs" and FIG. 6, can be conjugated to specific side chains in IBPs and other ice binding compounds. It is possible to use these methods for spin labeling any compound having similar properties as those disclosed herein.

Labeling Paramagnetic Ions to IBPs for DNP

Paramagnetic metal ions including those of transition, actinide, and lanthanide metals contain unpaired electron spins which can also be used to polarize nuclear spins through DNP. These ions may be attached to IBPs through chelating ligands. Chelating ligands are known to use more than one atom to bind to a metal ion to form an ion complex with high stability. For example, chelating agents like DTPA (pentetic acid, or diethylene triamine pentaacetic acid) and EDTA (ethylenediamine tetraacetic acid) or their derivatives, can easily complex $Gd^{3+}$. These ligands with chemical bonding to extra functional groups such as those described in FIGS. 1(A)-1(D) can be conjugated to specific side chains in IBPs and other ice binding compounds, resulting in paramagnetic ion labeled IBPs and compounds which can be used for DNP of frozen solutions.

The paramagnetic metal ions that can be used for DNP include, for example, lanthanide metals of atomic numbers 58-70, transition metals of atomic numbers 21-29, 42 and 44. Suitable paramagnetic ions include, for example, $Cr^{3+}$, $Mn^{2+}$, $Fe^{3+}$, $Fe^{2+}$, $Co^{2+}$, $Ni^{2+}$, $Cu^{2+}$, $Nd^{3+}$, $Sm^{3+}$, $Gd^{3+}$, $Tb^{3+}$, $Dy^{3+}$, $Ho^{3+}$, $Er^{3+}$ and $Yb^{3+}$.

A variety of chelating agents is known to form ion complexes. Generally, chelating agents often containing heteroatoms as electron pair donors, such as N and/or O, and may also contain P and/or S. DTPA, for example, is an often-used acyclic chelating agent. Its functional derivatives include DTPA-BMA, DTPA-BP, DTPA-BMEA, EOB-DTPA, BOPTA and MS-325. EDTA is another commonly used acyclic chelating agent. Its functional derivatives include EDTA-BMA, DPDP, PLED, HPTA, amides or diamides, such as TOGDA, sulphonates and phosphonates. Cyclic chelating agents may also be used for this purpose, and include, for example, cryptands, PCTA-[12], PCTP-[12], PCTP-[13], DOTA, DO3A and derivatives thereof, such as HP-DO3A and DO3A-butriol.

Paramagnetic metal ions of one or different metals may be used to make paramagnetic ionic spin-labeled IBPs and ice binding compounds (IBCs). The combinations of the organic radicals as discussed herein can also be attached to the same IBPs. The combination of the free radical spin-labeled IBPs and the paramagnetic ion labeled IBPs can also be used in a single solution for DNP.

Storage and shipment of the spin-labeled IBCs prepared according to the general methods disclosed herein would be readily apparent to any person having ordinary skill within the art. For example, the spin-labeled IBCs could be freeze dried and stored in airtight containers, preferably at −20° C. for prolonged shelf life.

DNP NMR may be performed according to standard procedures that would be readily apparent to any person having skill within the art. For example, a sample for analysis may be dissolved in, or otherwise homogeneously mixed with a spin-labeled IBC solution. After being frozen at low temperature, the DNP process for the sample may be performed followed by optional temperature variation and NMR procedure.

Likewise, imaging tissue structures, including cells, may also be performed according to standard procedures. For example, 41 of water of a spin-labeled IBC solution may be polarized through DNP at low temperature. Thereafter, the frozen solution may be promptly thawed to liquid state. Finally, the polarized solution may be injected into the tissue sample for analysis followed by an MM procedure. The spin-labeled IBC can also be filtered out leaving only water to be injected into the tissue.

For tissues, including cells, where low temperature may not cause serious damage to the structures, or where the structures at low temperature will be studied, tissues soaked with spin-labeled IBC, for example, through injection or diffusion, can be frozen directly at low temperature for DNP, which can be followed by optional temperature variation and then by an MRI procedure.

EXAMPLE 1

Figure 7:
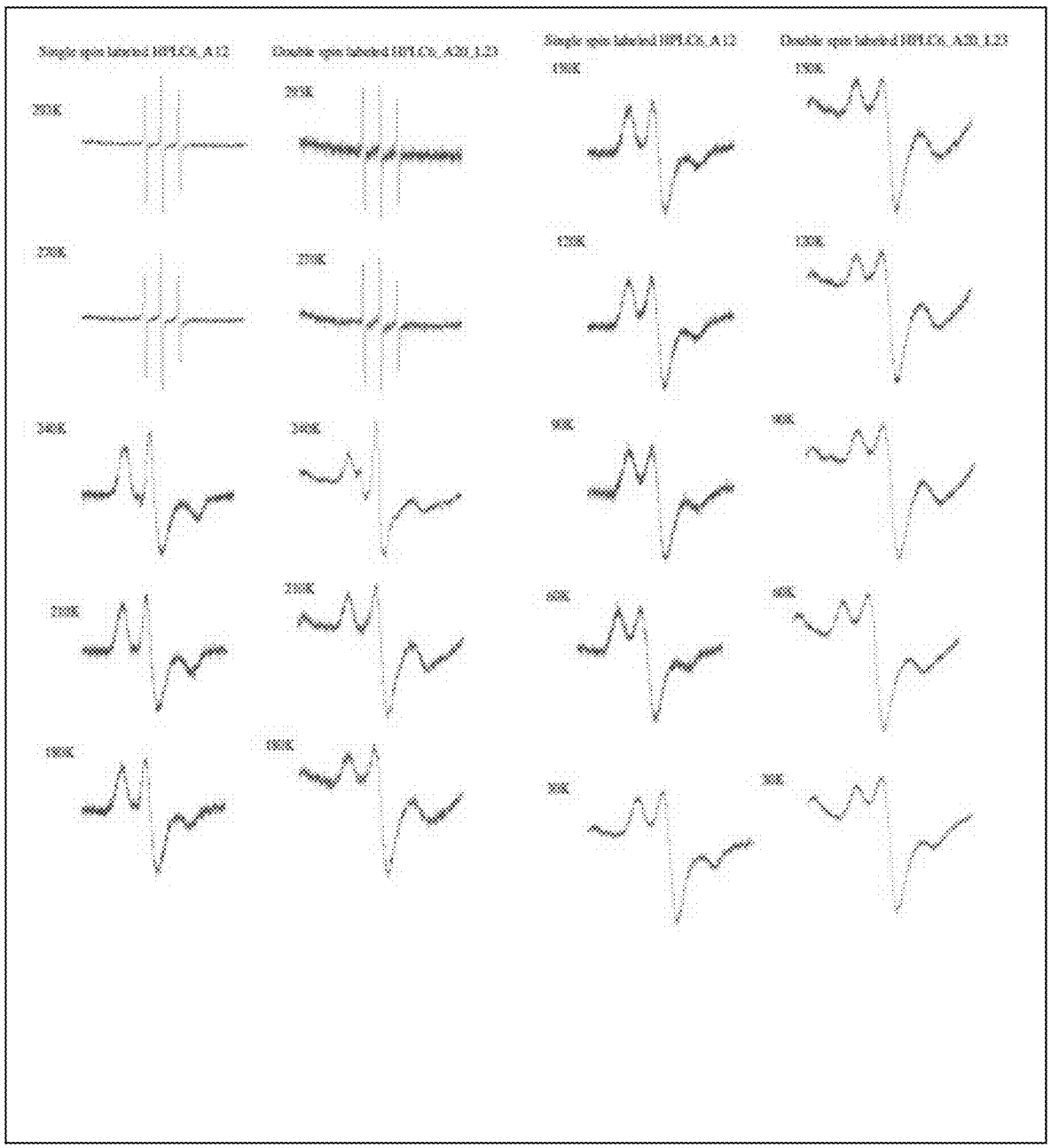
FIG. 7 shows EPR spectra of single spin-labeled HPLC6 _L12 and double spin-labeled HPLC6 A20C_L23C water solutions at different temperatures.

EPR Experimental Results of Single and Double Spin-labeled HPLC6 Peptides Using the IAP Reagent We have synthesized the single spin-labeled HPLC6_L12 and double spin-labeled HPLC6_A20C_L23C using the IAP reagent. The EPR spectra of their water solutions at different temperatures are shown in FIG. 7. The line shapes at the temperatures above the freezing points (298 K and 273 K) showed the typical triplet patterns of the nitroxide radicals. When the temperature was lowered below the freezing point, slow motion patterns of the line shapes began to appear, showing that the motions of the spin-labeled side chains are severely restricted after the spin-labeled IBPs were frozen in the ice matrices. The line shapes continued to become broader down to 90 K, indicating increased restriction of motions of the spin-labeling groups. Then, the line shapes stayed similarly at lower temperatures. These experiments indicate that 90 K could be sufficiently low enough to perform DNP experiments. It is important to note that the line shapes of the double spin-labeled IBP were broader than those of the single spin-labeled IBP at the same temperatures below the freezing point. This phenomenon shows the intramolecular spin-spin dipolar interactions of the double spin-labeled IBPs. As discussed above, these dipolar interactions facilitate the DNP mechanism of Cross Effect.

EXAMPLE 2

Using the Native Functional Groups of HPLC6 Isoform of Type I AFP

This AFP has the following sequence: Asp-Thr-Ala-Ser-Asp-<u>Ala</u>-Ala-Ala-Ala-<u>Ala</u>-Ala-Leu-Thr-Ala-Ala-Asn-Ala-Lys-Ala-Ala-<u>Ala</u>-Glu-Leu-<u>Thr</u>-Ala-Ala-Asn-Ala-Ala-Ala-Ala-<u>Ala</u>-Ala-Ala-Thr-Ala-Arg [SEQ ID NO:1], where the ice binding residues are underlined and the residues preferred for performing spin labeling are bolded. The bolded residues include lysine, arginine, glutamic acid and aspartic acid residues. Using these residues, single spin-labeled through spin labeling Lys or Arg side chain, double spin-labeled through spin labeling Lys and Arg side chain, and triple spin-labeled through spin labeling Asp, Asp and Glu side chains, etc., type I AFPs can be synthesized.

EXAMPLE 3

Using the Native Functional Groups of the QAEop12 Isoform of Type III AFP

This protein has the following sequence:

```
                                            [SEQ ID NO: 2]
MNQAS VVANQ LIPIN TALTL VMMRS EVVTP VGIPA
EDIPR LVSMQ VNRAV PLGTT LMPDM VKGYA A
``` where the residues involved in the putative ice binding surfaces are underlined and the available non-ice binding residues for performing spin labeling are bolded. They include lysine (K), arginine (R), glutamic acid (E), aspartic acid (D) and tyrosine (Y) residues. Using these side chains, single spin-labeled (using K or Y), double spin-labeled (using K and Y) and multiple spin-labeled (using R, R, R for making triple spin-labeled, using E, E, D, D for making quadruple spin-labeled, etc.) type III AFPs can be synthesized.

EXAMPLE 4

Functionalized DTPA Gd3+ Complex for Conjugation to IBPs

Figures 8A, 8B:
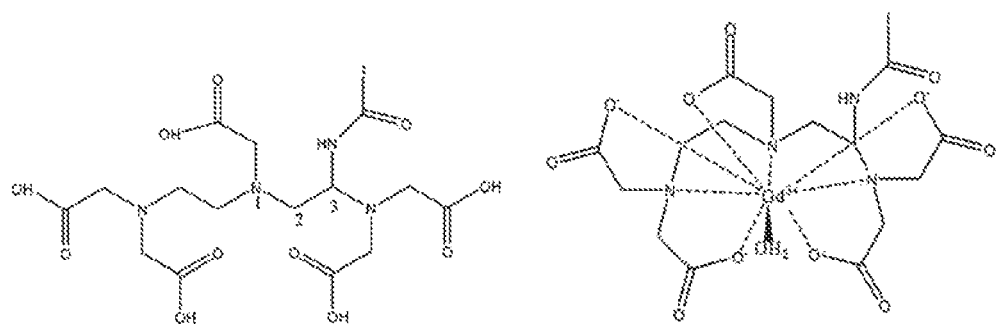
FIG. 8(A) shows the structure of 3-(2-iodoacetamide) DTPA.
FIG. 8(B) shows the structure of 3-(2-iodoacetamide) DTPA and its $Gd^{3+}$ complex.

As an example, we can synthesize 3-(2-iodoacetamido)-DTPA as shown in FIG. 8(A). The structure of its $Gd^{3+}$ complex is shown in FIG. 8(B). 3-(2-iodoacetamido)-DTPA can be easily conjugated to the Cys side chains of Cys substitution mutants of IBPs according to the chemistry described in section "Site Directed Spin Labeling" and shown in FIGS. 1(A)-1(D). Other functional groups as shown in FIG. 1(A) and FIG. 1(B) can also be chemically bonded to DTPA. Functional groups that can conjugate other functional side chains as exemplified in FIG. 6 may also be chemically bonded to DTPA.

---

What is claimed is:

1. A modified ice binding compound, comprising an ice binding compound having a functional group, and an electron spin label covalently bound to the ice binding compound through the functional group.

2. The modified ice binding compound of claim 1, wherein the ice binding compound comprises an antifreeze protein or a mutant thereof.

3. The modified ice binding compound of claim 2, wherein the ice binding compound comprises the antifreeze protein.

4. The modified ice binding compound of claim 3, wherein the antifreeze protein is selected from the group consisting of fish antifreeze glycoproteins (AFGP), type I, II, III and IV AFPs, insect AFPs, and plant AFPs.

5. The modified ice binding compound of claim 2, wherein the ice binding compound comprises the mutant of the antifreeze protein.

6. The modified ice binding compound of claim 5, wherein the mutant is a cysteine substitution mutant of the antifreeze protein.

7. The modified ice binding compound of claim 2, wherein the functional group is selected from the group consisting of an N-terminus, a C-terminus, and side chains of cysteine, serine, threonine, tyrosine, lysine, aspartic acid, glutamic acid, histidine, tryptophan and arginine residues.

8. The modified ice binding compound of claim 7, wherein the electron spin label comprises a paramagnetic metal ion, a nitroxyl radical, a trityl radical, and a bisdiphenylene-β-phenylallyl radical.

9. A kit comprising the modified ice binding compound of claim 1 and instructions for using the modified ice binding compound.

10. The kit of claim 9, further including a member of the group consisting of cyclodextrins, derivatives thereof, and combinations thereof.

11. A method of making a modified ice binding compound, comprising:
   a) reacting an electron spin label with an ice binding compound having a functional group to covalently bind the electron spin label to the functional group and form the modified ice binding compound; and
   b) purifying the modified ice binding compound.

12. The method of claim 11, wherein the ice binding compound comprises an antifreeze protein or a mutant thereof.

13. The method of claim 12, wherein the ice binding compound comprises the antifreeze protein.

14. The method of claim 12, wherein the ice binding compound comprises a cysteine substitution mutant of the antifreeze protein.

15. The method of claim 12, wherein the functional group is selected from the group consisting of an N-terminus, a C-terminus, and side chains of cysteine, serine, threonine, tyrosine, lysine, aspartic acid, glutamic acid, histidine, tryptophan and arginine residues, and the electron spin label comprises a paramagnetic metal ion, a nitroxyl radical, a trityl radical, and a bisdiphenylene-β-phenylallyl radical.

16. A method of studying molecules in a sample, comprising:
   a) dissolving or otherwise homogeneously mixing the sample for analysis with the modified ice binding compound of claim 1, and
   b) studying the molecules in the sample by magnetic resonance.

17. The method of claim 16, wherein the sample comprises a biological sample.

18. The method of claim 16, further comprising freezing the dissolved or homogeneously mixed sample for analysis and the modified ice binding compound, and optionally varying a temperature while studying the molecules by magnetic resonance.

19. A method of magnetic resonance imaging, comprising:
   a) freezing a solution of the modified ice binding compound of claim 1 and a solvent comprising water;
   b) thawing the solution;
   c) injecting the thawed solution into a tissue or tissue structure; and
   d) conducting an MM procedure on the tissue or tissue structure.

20. The method of claim 19, further comprising filtering the modified ice binding compound from the solution prior to injecting the thawed solution into the tissue or tissue structure.

* * * * *

SEQUENCE LISTING

```
<160> NUMBER OF SEQ ID NOS: 2

<210> SEQ ID NO 1
<211> LENGTH: 37
<212> TYPE: PRT
<213> ORGANISM: Unknown
<220> FEATURE:
<223> OTHER INFORMATION: Unknown fish

<400> SEQUENCE: 1

Asp Thr Ala Ser Asp Ala Ala Ala Ala Ala Ala Leu Thr Ala Ala Asn
1               5                   10                  15

Ala Lys Ala Ala Ala Glu Leu Thr Ala Ala Asn Ala Ala Ala Ala Ala
            20                  25                  30

Ala Ala Thr Ala Arg
        35

<210> SEQ ID NO 2
<211> LENGTH: 66
<212> TYPE: PRT
<213> ORGANISM: Unknown
<220> FEATURE:
<223> OTHER INFORMATION: Unknown fish

<400> SEQUENCE: 2

Met Asn Gln Ala Ser Val Val Ala Asn Gln Leu Ile Pro Ile Asn Thr
1               5                   10                  15

Ala Leu Thr Leu Val Met Met Arg Ser Glu Val Val Thr Pro Val Gly
            20                  25                  30

Ile Pro Ala Glu Asp Ile Pro Arg Leu Val Ser Met Gln Val Asn Arg
            35                  40                  45
```

```
Ala Val Pro Leu Gly Thr Thr Leu Met Pro Asp Met Val Lys Gly Tyr
    50              55                  60
Ala Ala
65
```